(12) United States Patent
Nizard et al.

(10) Patent No.: US 7,220,417 B2
(45) Date of Patent: May 22, 2007

(54) USE OF PHAEODACTYLUM ALGAE EXTRACT AS COSMETIC AGENT PROMOTING THE PROTEASOME ACTIVITY OF SKIN CELLS AND COSMETIC COMPOSITION COMPRISING SAME

(75) Inventors: Carine Nizard, Ivry sur Seine (FR); Bertrand Friguet, Paris (FR); Marielle Moreau, Marcq (FR); Anne-Laure Bulteau, Paris (FR); Alex Saunois, Orleans (FR)

(73) Assignee: LVMH Recherche, Paris (FR)

( * ) Notice: Subject to any disclaimer, the term of this patent is extended or adjusted under 35 U.S.C. 154(b) by 152 days.

(21) Appl. No.: 10/474,167

(22) PCT Filed: Apr. 2, 2002

(86) PCT No.: PCT/FR02/01129

§ 371 (c)(1),
(2), (4) Date: Oct. 3, 2003

(87) PCT Pub. No.: WO02/080876

PCT Pub. Date: Oct. 17, 2002

(65) Prior Publication Data

US 2004/0136945 A1      Jul. 15, 2004

(30) Foreign Application Priority Data

Apr. 3, 2001 (FR) .................. 01 04535

(51) Int. Cl.
*A61K 36/02* (2006.01)

(52) U.S. Cl. ............... 424/195.17; 424/401

(58) Field of Classification Search ............ None
See application file for complete search history.

(56) References Cited

U.S. PATENT DOCUMENTS 5,567,732 A * 10/1996 Kyle et al. .............. 514/560
6,432,468 B1    8/2002 Akimoto et al.

FOREIGN PATENT DOCUMENTS

| EP | 0 345 081 A2 | * | 12/1989 |
| EP | 0 646 647 | | 4/1995 |
| EP | 0 775 449 | | 5/1997 |
| JP | 59215386 A | | 12/1984 |
| JP | 07-224278 | * | 8/1995 |
| JP | 07224278 A | | 8/1995 |
| JP | 08040866 A | | 2/1996 |
| JP | 11049695 A | | 2/1999 |
| JP | 11-228381 | * | 8/1999 |
| JP | 2001048776 A | | 2/2001 |

OTHER PUBLICATIONS

Grima et al. (Journal of Applied Phycology (1996), vol. 8, pp. 359-367).*
Database Caplus 'Online! Chemical Abstracts Service, Columbus, Ohio, US; retrieved from STN Database accession No. 1995:890657 XP002187712 abstract & JP 07 224278 A (Sangyo Sozo Kenkyusho) Aug. 22, 1995.
Database WPI Week 198504 Derwent Publication Ltd., London, GB; AN 1985-021129 XP002187713 & JP 59 215386 A (Ind Res Inst of Japan) abstract.
Patent Abstracts of Japan vol. 009, No. 071 (C-272) & JP 59 204128 A (Kougiyou Kaihatsu Kenkyusho KK) abstract.
Patent Abstracts of Japan 07224278 A—Kikuchi Masako et al.
Patent Abstracts of Japan 59215386 A—Uchida Masaru.
Patent Abstracts of Japan 2001048776 A—Mekideche Nicole; English translation of corresponding French Patent Application, Publication No. 2 797 187.
Patent Abstracts of Japan 08040866 A—Miyazaki Toshitsugu et al.
Patent Abstracts of Japan 11049695 A—OkanoYuri et al.

* cited by examiner

Primary Examiner—Susan Coe Hoffman
(74) Attorney, Agent, or Firm—Millen, White, Zelano & Branigan, P.C.

(57) ABSTRACT

The invention relates to the use of an extract of the alga *Phaeodactylum*, particularly the alga *Phaeodactylum tricornutum*, as a cosmetic agent promoting the proteasome activity of skin cells, particularly keratinocytes, fibroblasts or melanocytes (preferably human).

The invention makes it possible to manufacture a cosmetic composition for protecting the skin from the adverse effects of UV exposure or for preventing and/or delaying skin ageing effects.

29 Claims, 2 Drawing Sheets

USE OF PHAEODACTYLUM ALGAE EXTRACT AS COSMETIC AGENT PROMOTING THE PROTEASOME ACTIVITY OF SKIN CELLS AND COSMETIC COMPOSITION COMPRISING SAME

The invention relates essentially to the use of an extract of the alga *Phaeodactylum*, particularly the alga *Phaeodactylum tricornutum*, as a cosmetic agent promoting the proteasome activity of skin cells, particularly keratinocytes, fibroblasts or melanocytes (preferably human), to a cosmetic composition containing it and to a method of cosmetic care.

The invention further relates essentially to the use of the extract of the alga *Phaeodactylum*, particularly *Phaeodactylum tricornutum*, in the manufacture of a cosmetic composition for protecting the skin from the adverse effects of UV exposure or for preventing and/or delaying the appearance of skin ageing effects.

Nowadays a large number of researchers are involved in the search for means of combating ageing in man. This is particularly the case in the field of cosmetics, where attempts are being made to combat, or at least delay, the appearance of apparent skin ageing effects such as wrinkles, loss of elasticity or skin color, etc.

More or less prolonged exposure to solar radiation, and mainly ultraviolet rays, is now well known for its adverse consequences in the medium or long term. Although the skin's pigmentation provides immediate protection from UVA (wavelength from 320 to 400 nanometers) as well as delayed protection from UVB (wavelength from 290 to 320 nanometers), prolonged exposure to ultraviolet rays can cause actinic erythema or solar elastosis, accelerate the appearance of skin ageing effects such as wrinkles, and sometimes even lead to the formation of a skin cancer. It is acknowledged that UVA, most of which passes through the epidermis, causes the production of oxidizing species such as free radicals, or reactive forms of oxygen, which react at various levels in the skin to damage the skin cells, particularly the keratinocytes, fibroblasts or melanocytes. This results in inflammatory manifestations or the appearance of actinic ageing, particularly in the form of wrinkles.

It has already been acknowledged for a long time that topical protection of the skin from UV rays is conventionally effected by using physical filters and/or chemical filters in sun products or products for combating ageing.

It is also known, from a publication by Friguet B. et al. in Ann. N.Y. Acad. Sci. 2000, 908, 143-54, entitled "Protein degradation by the proteasome and its implication in aging", that the proteasome is a multicatalytic protein complex known for its role in cell decontamination, its main function being to rid the cells of proteins damaged by oxidation. This elimination is accompanied by the formation of peptides, which are then metabolized by the cell. Thus the proteasome rids the cell of useless elements that hinder the optimal functioning of the cell by accumulating, as described by Petropoulos, Friguet et al. in Journal of Gerontol. Biol. Sci. 2000, 55A, no. 5, B220-B227, entitled "Increase of oxidatively modified protein is associated with a decrease of proteasome activity and content in aging epidermal cells".

One main object of the present invention is to solve the new technical problem that consists in the provision of a novel cosmetic agent capable of promoting the proteasome activity of skin cells, particularly keratinocytes, fibroblasts or melanocytes, preferably human.

Another main object of the present invention is to solve the new technical problem that consists in the provision of a novel cosmetic composition capable of protecting the skin from the adverse effects of UV exposure or of preventing and/or delaying the appearance of skin ageing effects.

Another object of the present invention is to solve the technical problem that consists in the provision of a means which complements that of protection by conventional UV filters, especially by assisting their action by becoming involved in the correct functioning of the cells, promoting their detoxication.

All these technical problems are solved by the present invention for the first time in a simple, inexpensive and reliable manner that can be used on the industrial scale in cosmetics.

Thus, according to a first feature, the present invention relates to the use of an extract of the alga *Phaeodactylum*, particularly the alga *Phaeodactylum tricornutum*, as a cosmetic agent promoting the proteasome activity of skin cells, particularly keratinocytes, fibroblasts or melanocytes (preferably human).

According to a second feature, the present invention further relates to the use of an extract of the alga *Phaeodactylum*, particularly the alga *Phaeodactylum tricornutum*, in the manufacture of a cosmetic composition for protecting the skin from the adverse effects of UV exposure or for preventing and/or delaying skin ageing.

According to a third feature, the present invention further covers a cosmetic composition promoting the proteasome activity of skin cells, particularly keratinocytes, fibroblasts or melanocytes, preferably human, or for protecting the skin from the adverse effects of UV exposure or for preventing and/or delaying skin ageing, characterized in that it comprises, as one of its cosmetic active agents, an extract of the alga *Phaeodactylum*, particularly the alga *Phaeodactylum tricornutum*, optionally in a cosmetically acceptable excipient, the skin care preferably being preventive care before exposure to UV rays or skin care after exposure to UV rays.

According to a fourth feature, the present invention further covers a method of cosmetic skin care, characterized in that it comprises the topical application, to the appropriate zones of the skin of a person in need thereof, of an effective amount of an extract of the alga *Phaeodactylum*, particularly the alga *Phaeodactylum tricornutum*, in order to obtain a preventive effect or a restorative effect, according to whether the topical application is effected before or after exposure to UV rays. The resulting overall effect is an anti-ageing effect on said zones of the skin, especially by improving the firmness and elasticity of the skin, delaying the appearance of wrinkles or reducing their depth.

Within the framework of any one of the features of the present invention, the extract of the alga *Phaeodactylum*, particularly the alga *Phaeodactylum tricornutum*, can be present in a cosmetic composition in a concentration of about 0.01% to 10%, particularly of about 0.1% to 5%, based on the total weight of the final cosmetic composition.

It is pointed out that the alga *Phaeodactylum*, particularly the alga *Phaeodactylum tricornutum*, is a diatomaceous alga originating from temperate climates. This alga is known for its high growth rate, enabling certain industries, such as the agri-foodstuffs industry, to use it as a rapid source of lipids for enriching a variety of products, or else as a food for aquaculture.

In a first embodiment, the extract is obtained by extraction with a polar extraction solvent and/or an apolar extraction solvent.

The extract of the alga *Phaeodactylum*, particularly the alga *Phaeodactylum tricornutum*, can be obtained especially by extraction with a polar extraction solvent and/or an apolar extraction solvent, particularly a $C_1$-$C_6$ alcohol or an aqueous-alcoholic mixture, a $C_2$-$C_6$ polyhydric alcohol such as ethylene glycol, a chlorinated solvent such as chloroform or dichloromethane, a $C_3$-$C_6$ ester of an organic acid, such as ethyl acetate, a $C_6$-$C_{10}$ alkane such as heptane, or a $C_5$-$C_8$ ether such as diisopropyl ether.

In one advantageous variant of the invention, this extract is obtained by extraction of the alga *Phaeodactylum*, particularly the alga *Phaeodactylum tricornutum*, with an alcohol or a water/alcohol mixture which has optionally been rendered alkaline, said alcohol being selected from the group comprising isopropanol, ethanol and methanol.

The chosen alcohol will advantageously be isopropanol or ethanol.

In general, the alga is advantageously frozen before any extraction operation. The freezing is preferably effected at a temperature of between about −40° C. and −20° C. and for a period preferably of between about 1 and 7 days. This prior step is advantageously used in order to produce a thermal shock on contact with the future extraction solvent so as to facilitate decantation from the silica (derived from the skeleton of the algal cells). The alga is then brought into contact with the extraction solvent.

In one advantageous variant, the frozen alga is immersed directly in the heated extraction solvent.

It is also advantageous to macerate the alga in the extraction solvent at room temperature.

In one advantageous variant, the alga is macerated at room temperature and preferably for a period of between about 5 minutes and 80 minutes, particularly preferably for a period of between about 20 minutes and 40 minutes.

In another advantageous variant, the extraction is carried out under reflux.

In yet another advantageous variant, the extraction can be carried out under an inert atmosphere, preferably under a nitrogen-saturated atmosphere. This makes it possible in particular to avoid pronounced oxidative degradation of the active molecules.

This extract is advantageously packaged under an inert gas such as nitrogen, and antioxidants can also be added in order to protect the active molecules.

In one advantageous variant, the amount of extraction solvent used is between about 0.1 liter and 20 liters, preferably between about 2 liters and 10 liters, per 100 g of alga, expressed by dry weight of alga.

In another advantageous variant, in the case of extraction with an alcohol or an aqueous-alcoholic mixture which has been rendered alkaline, the aforementioned algal extract is obtained after the following series of steps, some of which are described above:

a) the alga is frozen as described above and then immersed in the extraction solvent,
b) the alga is macerated,
c) the extraction solvent is rendered alkaline to a pH of between 10 and 14, preferably to a pH of 13, for example with aqueous sodium hydroxide solution or aqueous potassium hydroxide solution,
d) the insoluble materials are removed from the alcoholic or aqueous-alcoholic phase,
e) distilled water is added to the alcoholic or aqueous-alcoholic phase,
f) the resulting aqueous-alcoholic solution is washed by a liquid-liquid process with an apolar solvent that is immiscible with the alcoholic or aqueous-alcoholic phase, for example heptane, hexane or cyclohexane,
g) the phase containing the apolar solvent is removed,
h) the aqueous-alcoholic phase recovered after removal of the phase containing the apolar solvent is acidified to a pH of between 1 and 3, preferably to a pH of 2, for example with aqueous sulfuric acid solution or aqueous hydrochloric acid solution,
i) the solution obtained after acidification is subjected to a liquid-liquid extraction with an apolar solvent that is immiscible with the alcoholic or aqueous-alcoholic phase, for example heptane, hexane or cyclohexane,
j) the aqueous-alcoholic phase is then removed, and
k) the phase containing the apolar solvent, recovered after removal of the aqueous-alcoholic phase, is subjected to evaporation to give an oil free of apolar solvent, this oil being the desired extract according to the invention.

The use of an alcohol which has been rendered alkaline and then acidified makes it possible to obtain an extract with acceptable visual and olfactory characteristics in cosmetic compositions (yellow color and acceptable odor).

In a second advantageous embodiment of the invention, the aforementioned algal extract is obtained by extraction of the alga with supercritical $CO_2$. The use of this particular solvent implies that the alga has been lyophilized beforehand.

Other characteristics, objects and advantages of the present invention will become clearly apparent from the following explanatory description, which is given with reference to several Examples of the invention and to comparative activity tests, and Examples of the formulation of cosmetic compositions, which are given simply by way of illustration and cannot therefore in any way limit the scope of the invention.

Unless indicated otherwise, the proportions given in the Examples are expressed as percentages by weight. The temperature is in degrees Celsius and the pressure is atmospheric pressure.

EXAMPLE 1 OF THE INVENTION

Preparation of Extracts According to the Invention of the Alga *Phaeodactylum*, Particularly the Alga *Phaeodactylum tricornutum*

1.1) Extraction with a Polar Solvent, such as Isopropanol (IPA), by a First Process According to the preferred mode of carrying out the process, the whole of the extraction is carried out under an inert atmosphere (nitrogen saturation) in order to avoid pronounced degradation of the active molecules.

250 kg of biomass (*Phaeodactylum tricornutum*) are used in this Example.

This biomass, which is frozen at −20° C. and then immersed in isopropanol (IPA) refluxing at 80-83° C., with agitation. The thermal shock makes it possible to facilitate decantation from the silica (derived from the skeleton of the algal cells).

The amount of solvent used is 10 liters of IPA per liter of water contained in the biomass. Thus, for a percentage of dry matter of 30%, the aforementioned 250 kg of biomass are made up of 75 kg of dry matter and 175 kg of water. The amount of IPA used is 1750 kg in this case.

The whole (biomass+IPA) is refluxed for half an hour at about 80° C., with agitation, before being cooled to about 50° C.

After the biomass and IPA have been cooled to about 50° C., the whole is transferred to a GUEDU filter in order to separate the exhausted biomass from the algal extract solubilized in IPA.

The extract is concentrated in the batch reactor (concentration factor=71.5). The concentrated extract has an oily appearance.

This oily extract is then taken up in cold IPA at a rate of 10 kg of solvent per kg of oil. Agitation is continued for 20 minutes. The juice is then filtered (this makes it possible to remove the residual sticky sludge).

A decolorization and deodorization treatment is carried out in two batches in an 80 liter Schott reactor by the addition of zeolite and active charcoal, taking 30 minutes at room temperature. The amount of zeolite added (ABSENT 2000, supplied by UOP) is 0.94 kg and the amount of active charcoal added (CXV, supplied by CECA) is 1.6 kg. The ratio of charcoal to zeolite is 1.7.

The zeolite and charcoal are then removed by filtration on paper.

Antioxidants (DL-α-tocopherol at a final concentration of 0.05% by weight and ascorbyl palmitate at a final concentration of 0.05% by weight) are incorporated via a stock solution in IPA.

The filtrate containing the antioxidants is then concentrated by a batch process under an inert gas, such as nitrogen, until a brown oil is obtained.

This oil will hereafter be called extract E1 according to the invention of the alga *Phaeodactylum tricornutum*.

1.2) Extraction by a Second Two-Step Process, Polar Solvent/Ethanol, then Liquid-Liquid Extraction, Polar Solvent (Aqueous-Ethanolic), Apolar Solvent (Heptane)

The extraction starts with the dispersion of 49.8 kg of frozen dry mass derived from 250 kg of biomass (*Phaeodactylum tricornutum*), i.e. about 20% of dry mass, in 539 kg of 96% anhydrous ethanol rendered alkaline with 9 kg of 30.5% aqueous sodium hydroxide solution. After maceration for 30 minutes at the reflux point of the ethanol and under a nitrogen atmosphere, the whole is cooled to 18° C.

The insoluble materials are then separated off by filtration under nitrogen and removed.

151 kg of distilled water are added to the 573.9 kg of filtrate. This aqueous-alcoholic phase is agitated slowly for 10 minutes and is then washed with 162 kg of heptane by a liquid-liquid process. The heptane upper phase of the liquid-liquid partition is discarded. The lower phase is recovered because it contains the fatty acids in salt form due to the alkalization performed at the start of the extraction. The heptane washing operation is repeated two more times and the lower phase is systematically recovered.

The 720 kg of lower phase obtained in this way are acidified by the addition of 2.8 kg of sulfuric acid to bring the pH to a value of 2.2, thereby converting the fatty acids to the acid form. The whole solution is agitated for 10 minutes under nitrogen and is then subjected to a liquid-liquid extraction with an apolar solvent, said apolar solvent consisting in this case of a fraction of 158 kg of heptane. The heptane washing operation is repeated five times in order to recover a total of 697 kg of heptane phase derived from the five fractions containing the free fatty acids. This phase is evaporated to dryness on a rotary evaporator and then by molecular distillation to yield the active extract according to the invention in an amount representing 0.65 kg of oil.

The oil produced is a homogeneous liquid and is dark yellow in color.

This oil will hereafter be called extract E2 according to the invention of the alga *Phaeodactylum tricornutum*.

EXAMPLE 2

Evaluation of the Effect of an Extract according to the Invention, e.g. E2 of Example 1.2 above, as an Agent Promoting the Proteasome Activity of Human Skin Cells, Particularly Keratinocytes, in the Absence and Presence of UV Irradiation The extract of the alga *Phaeodactylum* used in the present Example is extract E2 obtained by the extraction process described above in the context of Example 1.2.

The studies described below were performed on normal human keratinocytes (NHK).

The action of extract E2 according to the invention on the skin cells is measured in two different ways, either on the basis of 3 proteolytic activities of the proteasome, or by evaluating the amount of oxidized proteins which have accumulated to a greater or lesser extent, as a function of the variation in proteasome activity.

1) Principle of the Tests 1.1) Measurement of the 3 Enzyme Activities Representing the Proteasome Activity The first type of measurement concerns three activities representing the proteasome: the chymotrypsin-like activity, the postglutamic hydrolase activity and finally the trypsin-like activity. They are furthermore carried by 3 different catalytic sites. Each peptidase activity of the proteasome is determined by using a fluorogenic peptide substrate specific for each of the activities, in the presence and absence of an inhibitor specific for the proteasome. The principle of the assay then consists in following, over time, the increase in fluorescence due to the release of the fluorophores derived from the fluorogenic peptides, using a spectrofluorimeter.

1.2) Measurement of the Amount of Oxidized Proteins

The second type of measurement is used as a complement to the enzyme activity measurements in order to evaluate the amount of oxidized proteins by a conventional method of detection. Said amount varies inversely with the proteasome activity, so this measurement makes it possible to measure the action of the cosmetic agent according to the invention on the proteasome activity.

The Oxyblot (Western blot) technique employed to detect the oxidized proteins is carried out in conventional manner, as described by Leammli U.K. in "Cleavage of structural protein during the assembly of the head of the bacteriophage T4", Nature, 1970, 277, 680-685.

The part relating to the immunodetection of the proteins on a membrane, employed in this well-known technique, was specially adapted as from the incubation with antibodies. It is described in 2.6).

In the case of UV exposure, primary cultures of human keratinocytes are irradiated with UVA and UVB at respective doses of 10 joules/cm$^2$ and 0.05 joule/cm$^2$. These values are constant for all the experiments.

1.3) Measurement of the Amount of Proteins (Proteasome)

In parallel with the activity measurements performed by Oxyblot, another protein detection technique is carried out in order systematically to determine the amount of proteins present in each aliquot of each sample. This technique is known by the name of Bradford's method. It is employed here in conventional manner, as described by Bradford M. in "A rapid and sensitive method for the quantitation of microgram quantities of protein utilizing the principle of protein-dye binding", Anal. Biochem. 72, 248 (1976). This technique is carried out systematically because of the experimental protocol chosen for the activity measurements. In fact, the experiments described below are performed on a constant amount of proteins with different aliquot volumes, which are then made up to 200 μl (constant total volume).

2) Materials and Methods 2.2) Culture of Normal Human Keratinocytes (NHK)

The cultures of normal human keratinocytes (NHK) are produced from samples of skin.

In a first step the sample is rinsed 4 times in PBS (Phosphate Buffered Saline—Sigma) (50 ml tubes). It is then decontaminated by being soaked in two successive baths of 70% ethanol for 3 seconds. When the sample has been decontaminated, it is placed in a Petri dish containing PBS. 1 mm wide strips are then cut out, care being taken to remove the maximum amount of adipose tissue and dermis. As they become available, the strips are placed in a Petri dish containing PBS. To be able to recover the keratinocytes from the epidermis, the strips are placed in a 25% solution of trypsin in PBS for 4 h at 37° C.

The dermis is then dissociated from the epidermis by scraping the strips with a scalpel, and the epidermal cells obtained are suspended in a tube containing DMEM (Dulbecco Modified Eagle's Medium—Gibco)+10% of FCS (Fetal Calf Serum—Eurobio). After homogenization of the suspension, the superficial part consisting of corneal cells is discarded and the remainder is filtered on a sieve.

The filtered part is centrifuged for 5 minutes at 176 g. The residue is taken up with NHK-D medium (DMEM+10% of FCS+0.4 μg/ml of hydrocortisone+10 ng/ml of EGF (Epidermal Growth Factor)+$10^{-9}$ M cholera toxin). The cells are counted and then inoculated at a rate of $15 \times 10^6$ cells/flask.

After 24 h of culture, the medium is changed, the cells are rinsed with PBS, and K-SFM proliferation medium (Gibco) is used for the remainder of the culture.

The keratinocytes are subcultured in completely conventional manner, but it is necessary to subculture them at 60-70% of confluence so that they retain their capacity to proliferate. Thus, when the cells are at 60-70% of confluence, the maintenance medium is discarded and the cellular mat is rinsed with PBS. The cells are brought into contact with 3 ml of a trypsin/EDTA solution; then, when the cells detach, the trypsin is inhibited with a medium containing 10% of FCS (Eurobio). The cellular suspension is homogenized, recovered and then centrifuged at 20 g for 5 minutes at room temperature. The resulting residue is taken up with medium only. For maintenance, inoculation is performed as above at a rate of $10^6$ cells/75 cm$^2$ in ventilated flasks kept under the conditions mentioned above. Confluence is obtained after about ten days and the cells can be amplified over 6 to 7 passes.

In cases where it is desired to test the activity of a substance on these keratinocytes, the tests will be performed on the culture medium containing keratinocytes, at the moment of confluence described above.

2.2) Lysis Buffer

Preparation of the lysis buffer first requires preparation of the following solutions:

⇒1.5 M Tris-HCl, pH=7.5

Dissolve 45.375 g of Tris base (Sigma; T1503) in 200 ml of distilled water, adjust the pH to 7.5 with 12 N HCl and then make up to 250 ml.

⇒1 M sucrose solution (Merck; ref. 7654)

Dissolve 8.55 g of sucrose in 25 ml of distilled water.

⇒2 mM MgSO$_4$ solution (Sigma; ref. M7506)

Dissolve 0.01 g of MgSO$_4$ in 20 ml of distilled water.

⇒4% Triton X100 solution (Sigma; ref. X100)

Dissolve 0.8 g of Triton X100 in 20 ml of distilled water, then divide into 0.5 ml aliquots and store at −20° C.

⇒40 mM PMSF solution (Sigma; ref. P7626)

Dissolve 14 mg of PMSF in 2 ml of absolute ethanol, divide into 50 μl aliquots and store at −20° C.

⇒0.5 mg/ml leupeptin solution (Sigma; ref. L2884; stored at −20° C.)

Divide into 50 μl aliquots and store at −20° C.

⇒1 M DL-dithiothreitol solution (Sigma; ref. D0632; stored at 4° C.)

Dissolve 0.154 g of DL-dithiothreitol in 1 ml of distilled water, divide into 10 μl aliquots and store at −20° C.

To prepare 100 ml of lysis buffer, it is first necessary to prepare the so-called incomplete solution described in Table 1, divide it into 4.39 ml aliquots (i.e. divide it into small volumes each equal to 4.39 ml) and store it at −20° C.:

TABLE 1

Incomplete solution for preparing the lysis buffer

| Solution | Volume | Final concentration |
|---|---|---|
| 1.5 M Tris-HCl pH = 7.5 | 0.33 ml | 5 mM |
| 1 M sucrose | 25 ml | 2.25 M |
| 2 mM MgSO$_4$ | 10 ml | 0.2 mM |
| 500 mM EDTA | 4 ml | 20 mM |
| Distilled water | 48.47 ml | |

The lysis buffer or so-called complete solution is prepared immediately before use with 4.39 ml of incomplete solution+500 μl of 4% Triton X100+10 μl of 1M DTT+50 μl of 0.5 mg/ml leupeptin+50 μl of 40 mM PMSF.

2.3) Assay of the Proteins by Bradford's Method

The procedure is conventional and requires the preparation of the following calibration range:

From a stock BSA solution: 50 μg/ml (BIORAD; standard protein; ref. 500-0006).

200 μl of Coomassie blue G250 are added to each tube.

Said blue is prepared immediately before use by dilution of the stock solution to 1/5.

To prepare the samples, cells are recovered from the lysis buffer and then sonicated before their protein concentration is assayed.

If the protein concentration of the samples is greater than 3 mg/ml, it is necessary to dilute them to 1/100 and then take 100 μl of cellular extract diluted with 700 μl of water and 200 μl of blue. If the concentration is low, it is then necessary to take 10 μl of cellular extract with 790 μl of water and 200 μl of Coomassie blue. The samples are vortexed. After a waiting time of 5 minutes, the results are read off at 595 nm on a BMG FLUOstar spectrofluorimeter. Said results are collated in Table 2.

TABLE 2

Assay of the proteins (Bradford's method): Calibration

| Amount of protein (μg/tube) | BSA (μl) | H$_2$O (μl) |
|---|---|---|
| 0 | 0 | 800 |
| 1 | 20 | 780 |
| 2 | 40 | 760 |
| 3 | 60 | 740 |

TABLE 2-continued

Assay of the proteins (Bradford's method): Calibration

| Amount of protein (µg/tube) | BSA (µl) | H₂O (µl) |
|---|---|---|
| 4 | 80 | 720 |
| 5 | 100 | 700 |
| 6 | 120 | 680 |
| 8 | 160 | 640 |

2.4) Preparation of the Samples for Testing 2.4.1) Preparation of the Samples for an Activity Assay The general principle of the culture, the treatment based on extract E2 and the irradiation with UVA and UVB is described in Scheme 1 at the end of the description. The NHK in culture according to 2.1) are recovered and lyzed according to 2.2) at different times, depending on the experiment envisaged, i.e. before or after treatment with the extract according to the invention and/or before or after UV irradiation. The proteasomes sought for analysis are present in the supernatant of these cellular lyzates.

The different types of sample are as follows:
I1=reference+extract E2 only
I2=reference+extract E2 before UV
I3=reference+extract E2 after UV Each volume of supernatant is divided into three aliquots each time and the aliquots of one and the same sample are placed on a microplate reader. The fluorogenic peptide substrates specific for each activity are added (as a function of the amount of proteins). The spectrofluorimeter manipulations described below are performed with a constant total volume, but with aliquots of different volumes Vi for each sample. Working with a constant amount of proteins for different Vi means that the amount of proteins introduced has to be checked first by Bradford's method described in 2.3).

The aim is then to report an amount of proteins present per mg of proteins introduced.

2.4.2) Preparation of the Samples for an Assay to Measure the Amounts of Oxidized Proteins The general culture principle applied is the same as that described in Scheme 1. The Oxyblot (Western blot) technique, or protein electrophoresis, causes the samples Ii to migrate on the gel. They are then transferred to a membrane, which is incubated with the desired antibody. To measure the amount of oxidized proteins, an incubation is carried out with an anti-dinitrophenyl (anti-DNP) polyclonal antibody in order to detect the carbonyl groups of the proteins which have reacted before performing the activity test.

2.5) Assay of the Enzyme Activities of the Proteasome a) Introduction

To assay the enzyme activities of the proteasome, the cultivated NHK are rinsed twice with PBS and each peptidase activity of the proteasome is then determined by using a fluorogenic peptide substrate specific for each of the activities, in the presence and absence of an inhibitor specific for the proteasome, namely MG132 (N-Cbz-Leu-Leu-leucinal). The peptide substrates are as follows: Leu-Leu-Val-Tyr-aminomethylcoumarin (LLVY-amc) for the chymotrypsin-like activity, Leu-Leu-Glu-β-naphthylamine (LLE-na) for the postglutamic hydrolase activity and Leu-Ser-Thr-Arg-amc (LSTR-amc) for the trypsin-like activity. The principle of the assay consists in following, over time, the increase in fluorescence due to the release of the fluorophores aminomethylcoumarin (amc) or β-naphthyl-amine (na) derived from the fluorogenic peptides, using a spectrofluorimeter.

To measure the effect of UV on the proteasome, normal human keratinocytes, or NHK, in culture are irradiated with constant doses of 10 J/cm² of UVA and 0.05 J/cm² of UVB, after which they are recovered and lyzed at different times following irradiation.

b) The Three Proteolytic Activities of the Proteasome

The chymotrypsin-like, postglutamic hydrolase and trypsin-like activities are measured on proteasomes extracted from the cellular lyzates using the fluorogenic peptides as substrates at the following concentrations: LLVY-amc at 12.5 µM, LLE-na at 150 µM and LSTR-amc at 40 µM. For each series of measurements, it is necessary to carry out another incubation with the fluorescent substrate specific for each activity. These activities are measured in parallel with an inhibitor specific for the proteasome, namely MG132 (N-Cbz-Leu-Leu-leucinal) at 20 µM, in order to evaluate the proportion of activity that is independent of the proteasome.

2.5.1) Procedure for Determining the LLVY (Chymotrypsin-Like) Activity

The principle of this procedure, which is given below, is identical for the three activities, except for the reagents.

The so-called "chymotrypsin-like" enzyme activity is the activity similar to that of chymotrypsin, which is represented by a cleavage after an aromatic amino acid, in this case tyrosine.

N-succinyl-LLVY-amc 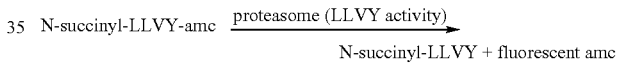 N-succinyl-LLVY + fluorescent amc

The fluorogenic pigment is released by a cleavage reaction. Thus, in a first step, the crude results, expressed in fluorescence units per minute (FU/min), can be obtained by reading the spectrofluorimeter (FLUOstar (BMG)). The fluorescence unit is a function of the apparatus used and is therefore arbitrary.

We arbitrarily chose to express the proteasome activity in pmol of amc released per min and per mg of proteins (proteasome) present in the sample. To do this, the amount of proteins (proteasome) is first assayed by Bradford's method in each sample taken from the NHK cultures. The experiments are performed with different volumes Vi, only the total reaction volume remaining constant at 200 µl. An amc calibration curve is also established beforehand so as to be able to correlate the results yielded by the apparatus on a given sample Ii with those for which the amount of proteins is known.

The following reagents are used for this purpose:
25 mM TRIS buffer, pH 7.5
for the calibration curve: 7-amino-4-methylcoumarin (amc) (Sigma: A9891) 20 mM stock solution (3.5 mg/1 ml DMSO)
for the activity measurement: fluorogenic substrate: N-succinyl-Leu-Leu-Val-Tyr-7-amino-4-methylcoumarin (Sigma: S6510) 10 mM stock solution in DMSO An amc calibration range is prepared by diluting the amc stock solution to 4 µM in TRIS buffer. Each amount is distributed in duplicate into a 96-well plate.

Run a blank with 200 µl of TRIS buffer. Then read off the results on the spectrofluorimeter at an excitation wavelength of 350 nm and an emission wavelength of 440 nm.

The results obtained for the calibration curve (line of slope a) are collated in Table 3 below:

TABLE 3 amc calibration curve

| Amount of amc (µM) | amc (µl) | TRIS (µl) |
|---|---|---|
| 0 | 0 | 200 |
| 0.1 | 5 | 195 |
| 0.2 | 10 | 190 |
| 0.3 | 15 | 185 |
| 0.4 | 20 | 180 |
| 0.5 | 25 | 175 |
| 0.6 | 30 | 170 |
| 0.7 | 35 | 165 |
| 0.8 | 40 | 160 |
| 1.0 | 50 | 150 |

To assay the LLVY activity, a fixed volume of cellular lyzate (determined by Bradford's method so that the same amount of proteins is ultimately introduced each time) is introduced in duplicate into a 96-well plate. In practice, this is the lowest protein concentration of the samples (which must correspond to 20 µg of proteins). The volume is made up to 100 µl with TRIS buffer.

The samples are then incubated, 100 µl of the fluorogenic peptide substrate for the LLVY activity being added, having first been diluted to 25 µM in TRIS buffer (for a final concentration of 12.5 µM).

The results are then read off on the spectrofluorimeter at an excitation wavelength of 355 nm and an emission wavelength of 460 nm, with a gain of 40, every 2 minutes for 30 minutes.

The crude results are expressed in FU/min, this unit being a function of the apparatus.

The assay is performed on a constant reaction volume of 200 µl containing a volume Vi of cellular lyzate that is fixed as a function of the protein (proteasome) concentrations of the lyzates.

The concentration of the proteins assayed immediately before use is expressed in µg/µl.

Based on the calibration range, the activity can be expressed in pmol of amc released per minute and per mg of proteins by using the following empirical formula:

$$\frac{\text{mean rate in FU/min (value supplied for apparatus)} \times 200 \times 10^{-6} \times 10^{-6} \times 10^{12}}{\text{µg/µl of protein (measured by Bradford's method)} \times Vi \cdot 10^{-3} \times \text{coefficient of slope } a \ (a = 4.568 \cdot 10^4)}$$

For each sample Ii divided into aliquots, it is sought to determine the amount of amc released and to express it in pmol/min/mg of protein. This is done using the calibration curve. The quotient of the magnitude read off on the spectrofluorimeter and the slope of said curve gives us a first intermediate result expressed in µmol/l/min of proteins. It then suffices to multiply this value by the final reaction volume (200 µl) and divide by the volume Vi of the aliquot of the sample Ii to be assayed, and by the amount of proteins (µg) assayed immediately before use by Bradford's method.

The final result can then be expressed, except for the adjustment factors, in pmol/min/mg of proteins.

Ri=(N.Vt/Vi.Qi).coefficient

N=number of moles of proteins released per liter and per minute

Vt=final reaction volume (200 µl)

Vi=volume of an aliquot for the sample Ii (µl)

Qi=amount of proteins (µg) assayed by Bradford's method

If the formula described above is applied, Ri represents the amount of proteins (proteasome) sought, arbitrarily expressed in pmol/min/mg of proteins (proteasome) introduced.

2.5.2) Procedure for Determining the LSTR Activity (Trypsin-like Activity)

The following cleavage reaction is studied:

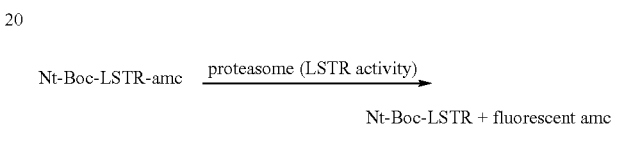

Nt-Boc-LSTR-amc $\xrightarrow{\text{proteasome (LSTR activity)}}$ Nt-Boc-LSTR + fluorescent amc The LSTR activity can be obtained with an identical formula by first carrying out an amc calibration using the following reagents:

25 mM TRIS buffer, pH 7.5 for the calibration curve: 7-amino-4-methylcoumarin (amc) (Sigma: A9891) 20 mM stock solution (3.5 mg/1 ml DMSO)

The crude results are read off on the spectrofluorimeter set at an excitation wavelength of 350 nm and an emission wavelength of 440 nm.

for the activity measurements: fluorogenic substrate: N-t-Boc-Leu-Ser-Thr-Arg-7-amino-4-methylcoumarin (Sigma: B4636) 10 mM stock solution in DMSO proteasome inhibitor: MG132 (Z-Leu-Leu-Leu-CHO) (Affinity, ZW8440) 20 mM stock solution in DMSO The results obtained for the calibration curve (line of slope b) are collated in Table 4 below:

TABLE 4 amc calibration curve

| Amount of amc (µM) | amc (µl) | TRIS (µl) |
|---|---|---|
| 0 | 0 | 200 |
| 0.1 | 5 | 195 |
| 0.2 | 10 | 190 |
| 0.3 | 15 | 185 |
| 0.4 | 20 | 180 |
| 0.5 | 25 | 175 |
| 0.6 | 30 | 170 |
| 0.7 | 35 | 165 |
| 0.8 | 40 | 160 |
| 1.0 | 50 | 150 |

For the activity measurements, the results are read off on the FLUOstar (BMG) at 355 nm (excitation wavelength) and 460 nm (emission wavelength), with a gain of 30, every 2 min for 30 min.

The results can also be obtained with another empirical formula similar to the previous one:

$$\frac{\text{mean rate in FU/min (value supplied for apparatus)} \times 200 \times 10^{-6} \times 10^{-6} \times 10^{12}}{\mu g/\mu l \text{ of protein (measured by Bradford's method)} \times Vi \cdot 10^{-3} \times \text{coefficient of slope } b \ (b = 1.728 \cdot 10^4)}$$

2.5.3) Procedure for Determining the LLE Activity (Postglutamic Hydrolase Activity)

The following cleavage reaction is studied:

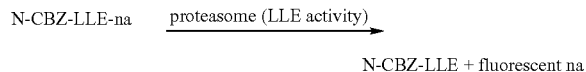

N-CBZ-LLE-na $\xrightarrow{\text{proteasome (LLE activity)}}$ N-CBZ-LLE + fluorescent na A calibration is carried out according to the same scheme, this time relative to the substrate β-naphthylamine (na) using the following reagents:

25 mM TRIS buffer, pH=7.5 for the calibration curve: βnaphthylamine (na) (Sigma: N8381) 20 mM stock solution (5.73 mg/2 ml DMSO)

The results are read off on the spectrofluorimeter at an excitation wavelength of 333 nm and an emission wavelength of 410 nm.

The results obtained for the na calibration curve (line of slope c) are collated in Table 5 below:

TABLE 5

| Amount of na (μM) | na calibration curve | |
|---|---|---|
| | na (μl) | TRIS (μl) |
| 0 | 0 | 200 |
| 0.1 | 5 | 195 |
| 0.2 | 10 | 190 |
| 0.3 | 15 | 185 |
| 0.4 | 20 | 180 |
| 0.5 | 25 | 175 |
| 0.6 | 30 | 170 |
| 0.7 | 35 | 165 |
| 0.8 | 40 | 160 |
| 1.0 | 50 | 150 | for the activity measurements: fluorogenic substrate: N-CBZ-Leu-Leu-Glu-β-naphthylamine (Sigma: C0788) 10 mM stock solution in DMSO The measurements are read off on the FLUOstar apparatus (BMG) at 340 nm (emission wavelength) and 410 nm (excitation wavelength), with a gain of 83, every 2 minutes for 35 minutes.

Using the same procedure as for the previous activities, a measure of the LLE activity is then obtainable with the following empirical formula, in which the amount of protein (proteasome) is expressed in pmol of na released/minute/mg of proteins (proteasome) introduced:

$$\frac{\text{mean rate in FU/min (value supplied for apparatus)} \times 200 \times 10^{-6} \times 10^{-6} \times 10^{12}}{\mu g/\mu l \text{ of protein (measured by Bradford's method)} \times Vi \cdot 10^{-3} \times \text{coefficient of slope } c \ (c = 0.966 \cdot 10^4)}$$

2.6) Detection of the Amount of Accumulated Oxidized Proteins 2.6.1) Detection by OXYBLOT (Western Blot)

The aim is to detect the carbonyl groups (oxidation markers) which have been introduced into the protein chains via species sensitive to the action of oxygen (ROS=Reactive Oxygen Species) or else to other oxidation mechanisms such as glycation/glycoxidation or lipoperoxidation, according to a site-specific mechanism.

The principle is as follows. The carbonyl groups in the chains react with 2,4-dinitrophenylhydrazine (DNPH) to give a hydrazone derivative. The samples labeled with DNP are separated by electrophoresis on a polyacrylamide gel and then transferred to a nitrocellulose membrane, as for a conventional Western blot. The membrane is then incubated in the presence of the first antibody specific for the DNP molecule bonded to the proteins possessing a carbonyl group. The next step is incubation with the secondary (anti-rabbit) antibody coupled with peroxidase. Disclosure is effected with the reagents described in 2.6.2).

2.6.2) Protocol

All the reagents used originate from the OXYBLOT kit (Appligene-Oncor, Illkirch, France).

A—Preparation of the Samples and Electrophoresis

We use between 15 and 20 μg of proteins originating from 5 μl of irradiated or non-irradiated keratinocyte lyzates. 10 μl of 2,4-dinitrophenylhydrazine and 5 μl of 12% SDS are added and the reaction is then left to proceed for 15 min at room temperature. 7.5 μl of neutralizing solution (solution supplied in the kit) are subsequently added. The samples are then ready to be deposited.

The low-molecular proteins are subjected to electrophoresis on a 1 mm thick polyacrylamide gel at a concentration of 12.5%, under denaturing and reducing conditions, in a discontinuous buffer, by Laemmli's method (1970). Gels containing 12.5% of T (T=acrylamide+bis-acrylamide) and 2.7% of C (C=(bis-acrylamide/acrylamide)+bis-acrylamide) make it possible to separate the proteins with molecular weights varying from 20 to 120 kDa. The apparatus employed originates from Hoefer. All the solutions required to develop the gels are given below:

I) Buffers and Solutions Used to Prepare the Electrophoresis Gels under Denaturing and Reducing Conditions in a Discontinuous Buffer Monomer solution: 40% acrylamide/bis-acrylamide, 2.6% C (Biorad; ref. 161-0148)

Resolving gel buffer: 1.5 M Tris-HCl, pH=8.8

Dissolve 18.15 g of Tris base (Sigma; T1503) in 100 ml of distilled water and adjust the pH to 8.8 with 12 N HCl.

Stacking gel buffer: 0.5 M Tris-HCl, pH=6.8

Dissolve 6 g of Tris base in 100 ml of distilled water and adjust the pH to 6.8 with 12 N HCl.

10× migration buffer: 0.25M Tris-HCL, pH=8.3; 1.92 M glycine; 1% SDS

The following reagents are used: 12 g of Tris base, 57.6 g of glycine (Research Organics Inc.; 5037G), 40 ml of 10% SDS (Sigma; L5750), and the volume is made up to 400 ml with distilled water.

These solutions are stored at 4° C.

Ammonium persulfate, $(NH_4)_2S_2O_8$: (Sigma; A1433) at a concentration of 10%, i.e. 100 mg/ml. The solution is divided into aliquots and stored at −20° C.

4× reducing sample buffer: 2.5 ml of 0.25 M Tris-HCl, pH=6.8; 0.4 g of 8% SDS; 2 ml of 40% glycerol; 1 ml of 20% β-mercaptoethanol; a spatula tip of 0.02% bromophenol blue. This solution is stored at room temperature.

Prestained standards of low molecular weights (Biorad; ref. 161-0305). These are composed of phosphorylase B (104 kDa), bovine serum albumin (82 kDa), ovalbumin (48.3 kDa), carbonic anhydrase (33.4 kDa), soybean trypsin inhibitor (28.3 kDa) and lysozyme (19.4 kDa).

II) Electrophoresis Gels

Preparation of the Resolving Gel Containing 12.5% of T

TABLE 6

| Solution | Volume for one gel (10 ml) | Final concentration |
| --- | --- | --- |
| Monomer solution | 3.12 ml | T; 2.7% C |
| Resolving gel buffer | 2.5 ml | 0.375 M |
| 10% SDS | 100 µl | 0.1% |
| Ammonium persulfate (10%) | 70 µl | 0.07% |
| TEMED (Research Organics Inc.; 3009T) | 10 µl | |
| Distilled water | 4.2 ml | |

Preparation of the Stacking Gel Containing 4% of T

TABLE 7

| Solution | Volume for two gels (10 ml) | Final concentration |
| --- | --- | --- |
| Monomer solution | 1 ml | T; 2.7% C |
| Resolving gel buffer | 2.5 ml | 0.175 M |
| 10% SDS | 100 µl | 0.1% |
| Ammonium persulfate (10%) | 70 µl | 0.07% |
| TEMED (Research Organics Inc.; 3009T) | 10 µl | |
| Distilled water | 4.2 ml | |

Preparation of the Separating Gel

This gel can be poured either the day before or the same day, but at any event two hours before migration.

Two gels can be poured into the mold used. The set-up is constructed by stacking the following in succession: the red seals, the greased black seals, a piece of plastic, a large plate, a piece of plastic, an alumina plate, the spacers (white for the 1 mm gels; black for the 1.5 mm gels), a glass plate, a piece of plastic, an alumina plate, the spacers, a glass plate, three pieces of plastic and then the cover. The resulting set-up is held together with clips and placed on a flat area.

The gel is poured using a P5000 pipette up to about 0.5 mm from the bottom of the comb provided for the stacking gel. The comb is removed and water is then added very gently so that the gels are flat (±0.5 ml of water/gel).

The set-up is covered with aluminum and must not be moved during polymerization.

Preparation of the Stacking Gel

The separating gels (between the alumina and glass plates) are removed from the mold and placed on the electrophoresis apparatus. If there is only one gel, this must be replaced with a glass plate.

The comb is inserted between the alumina plate and the glass plate. The gel is then poured with a Pasteur polyethylene transfer pipette (Biorad, ref. 223-9528). Before polymerization, the level of the gel is checked and adjusted if the sample volume is high. The gel polymerizes in one hour.

Preparation of the Samples

Before the cells contained in the dishes are recovered, they are rinsed twice with PBS. After the last rinse, the PBS is removed as far as possible. The cells are recovered in lysis buffer (cf. Scheme 1) by scraping (minimum of $5.10^6$ cells/ml of lysis buffer). The lyzates are frozen at −80° C.

Before being deposited, the thawed lyzates are sonicated and the proteins in said sample are then assayed.

The volume to be deposited depends on the amount of proteins (maximum amount of proteins: 60 µg; max. vol.=25 µl, min. vol.=5 µl). Following the preliminary tests, the volume of each sample deposited corresponds to 10 µg of proteins.

The proteins were assayed while the separating gel was polymerizing.

Deposits 250 ml of migration buffer are poured onto the gel, between the gel, the glass plate and the electrophoresis apparatus, and into the tank.

The samples are subsequently centrifuged at 10,000 g for 5 min and then deposited. 10 µl of prestained standards (Biorad, Prestained SDS-PAGE standards, ref. 161-0305) are also deposited, together with 0.3 µg of HSP32 (TEBU, ref. SPP-730, divided into 0.1 µg/ml aliquots and frozen at −20° C.).

Migration

Electrophoresis is carried out at room temperature, under refrigeration, with a non-limiting voltage of 300 V and with a constant amperage (15 mA) during migration in the stacking gel. The amperage is reduced to 10 mA once the samples have reached the separating gel.

Electrophoresis is stopped when the migration front reaches the bottom of the gel (about 1 hour 30 minutes of migration).

B—Transfer of the proteins onto a membrane and blocking of the specific binding sites When migration has finished, the gel is equilibrated for 20 minutes at room temperature, with agitation, in the transfer buffer on which this method is based, said buffer being described by Towbin H., Staehelin T. and Gordon J. in "Electrophoretic transfer of proteins from polyacrylamide gels to nitrocellulose sheets: procedure and some applications", Proc. Natl. Sci., USA 1979, 76, 4350-4354.

A polyvinylidene difluoride (PVDF) membrane (Biorad, ref. 162-0184), with a good mechanical strength and a high protein fixing capacity, is soaked in 100% methanol until it is transparent, and then equilibrated in the transfer buffer until it is completely immersed (20 min).

A thick sheet of filter paper (Biorad, ref. 17033960) previously soaked in the transfer buffer, the PVDF membrane and the gel are introduced into the semi-dry transfer apparatus (Biorad) and another wetted sheet of filter paper is then placed on the anode. Care must be taken to ensure that all air bubbles between the different layers are removed using a glass rod so as to avoid any risk of transfer. The apparatus is then closed with a cover acting as the cathode.

The proteins are transferred at a non-limiting amperage (5.5 mA/cm$^2$, 250 mA) and at a constant voltage (15 V) for 30 minutes.

The membrane is then placed overnight at 4° C., with agitation, in a solution for blocking the specific binding sites, consisting of 10% (25 g) of skimmed milk (Régilait) in TBS-T buffer (25 ml).

C—Antigen-Antibody Reaction: Immunodetection of the Proteins on a PVDF Membrane

The ECL (Enhanced ChemiLuminescence) kit is used to disclose the peroxidase with the aid of its substrate.

After blocking of the non-specific sites, the membrane is rinsed once for 15 minutes and twice for 5 minutes in TBS-T.

This membrane is then brought into contact with the anti-DNP rabbit primary antibody diluted to 1/150, for one hour at room temperature, with agitation.

It is then rinsed once for 15 minutes and twice for 5 minutes in TBS-T to remove the excess free antibody that has not been fixed.

It is then brought into contact with the peroxidase-coupled anti-rabbit secondary antibody (Amersham; ref. NA934; stored at 4° C.) diluted to 1/5000 in TBS-T (5 ml), at room temperature, with agitation.

After one hour of incubation, it is quickly rinsed twice with TBS-T buffer and then washed once for 15 minutes and finally four times for 5 minutes with TBS-T buffer.

After draining, it is placed on a food-grade film (SARAN) with the protein side, i.e. upwards.

The membrane is developed with a high-sensitivity detection kit by chemoluminescence (Amersham; ECL Western blotting, ref. RPN2106) using luminol as the peroxidase substrate. Under the action of peroxidase and an amplifier, the luminol is oxidized and passes to an excited transient state. It returns to the ground state by emitting photons, which then interact with an autoradiographic film placed on the membrane.

1 ml of each of the two solutions of the detection kit are mixed (2 ml, minimum volume required to cover the membrane).

The mixture is immediately poured uniformly over the membrane and left in contact with it for exactly one minute at room temperature.

The drained membrane is protected under a Saran food-grade film, placed in a cassette protected from the light, and then covered with a preflashed autoradiographic film (Amersham, Hyperfilm ECL, ref. RPN2103).

After one hour of exposure, the autoradiographic film is recovered, immersed for 5 minutes in a film developer (radio developer, LX 24, Kodak), then rinsed with water and finally fixed by immersion for a minimum of 5 minutes in the fixative (radio fixative, AL 4, Kodak) before being rinsed with water again.

The film is dried and the bands recorded are quantified using the software Gels Analysts 3.01.

3) Results of the Tests 3.1) Effects of Extract E2 according to the Invention on the Activities of the NHK Proteasome The samples used here were prepared according to the protocol described in Scheme 1 for the reference and for the sample treated with the extract according to the invention. A 15 µl aliquot is taken and activity measurements are made according to 2.5).

The results given in Tables 8, 9 and 10 show that, 7 hours after the addition of the algal extract (Ph) according to the invention, the 3 peptidase activities of the proteasome increase, this increase being significant for 2 of them (the chymotrypsin-like and trypsin-like activities). Furthermore, it is observed that, in the NHK treated with Ph for 7 hours, the amount of intracellular oxidized proteins is smaller than for the reference cells (FIG. 4, lanes 1 and 2). This shows that the observed stimulating effect of the extract according to the invention on the peptidase activities of the proteasome is represented by a decrease in the proportion of intracellular oxidized proteins. In practice, this test was performed on an 8 µg aliquot of cellular lyzate. The 3 types of sample, I1, I2 and I3, were prepared 7 hours after irradiation and then incubated in the presence of DNPH for 15 min. The reaction was then stopped with a neutralizing solution supplied in the Amersham kit.

3.2) Effects of UVA+UVB on the Proteasome of NHK in Primary Culture

Primary cultures of human keratinocytes according to 2.1) were irradiated with UVA and UVB according to a protocol corresponding to the principle of Scheme 1. The dose of ultraviolet rays chosen for this study is 10 joules/cm$^2$ for UVA and 0.05 joule/cm$^2$ for UVB. Following combined irradiation with these two doses of UVA and UVB, the three peptidase activities of the proteasome are measured at different times. For this assay the cells are lyzed 1 hour, 3 hours, 7 hours and 24 hours after irradiation, and the protein (proteasome) concentration is determined according to 2.3). The activity measurements are made according to 2.5) with fluorogenic substrate concentrations of 12.5 µM for LLVY-amc, 150 µM for LLE-na and finally 40 µM for LSTR-amc. These activities were measured in parallel with MG132 (20 µM) in order to evaluate the proportion of activity that was independent of the proteasome. The results given in FIGS. 1, 2 and 3 are expressed in % relative to the non-irradiated reference, and show that the three peptidase activities are reduced for the four times analyzed after UVA+UVB exposure. This experiment demonstrates that the activity of the proteasome is affected following irradiation with ultraviolet rays. It is also seen that the effect is the greater, the longer the time separating the irradiation from the activity measurement (7 h and 24 h).

3.3) Effects of an Extract of the Alga Ph on the Proteasome Activities of NHK when it is Administered before UVA+UVB Irradiation It was necessary to add antioxidizing vitamins (50 µM tocopherol and 1 mM ascorbyl phosphate) in order to preserve the efficacy of extract E2 during and after irradiation. Primary cultures of human keratinocytes according to 2.1) were treated with the extract according to the invention (dose of 5 µg/ml+vitamins) for 48 hours, then irradiated with UVA+UVB and finally lyzed. The results contained in Tables 11, 12 and 13 below show that the drop in the peptidase activities of the proteasome following irradiation with UVA+UVB is completely blocked in the presence of the extract according to the invention to which vitamins have been added. As the level of peptidase activities of the proteasome was the same for the untreated/non-irradiated reference NHK as for the treated/irradiated NHK 24 h later, the cosmetic agent based on the extract according to the invention allowed the peptidase activities of the proteasome to be preserved, so it has a protective effect against UVA+UVB.

3.4) Effects of an Extract of the Alga *Phaeodactylum*(Ph) on the Proteasome Activities of NHK after Irradiation Primary cultures of human keratinocytes are irradiated with the dose of UVA and UVB and then treated for 7 hours with 2.5 µg/ml of extract E2 according to the invention. It is seen that the amount of intracellular oxidized proteins is increased by UV irradiation, but to a lesser extent when the cells have been treated with extract E2 according to the invention. The experiment is described in 3.1) and the results are shown in FIG. 4 (lanes 3 and 4). The use of said extract allows a better removal of the oxidized proteins. Also, the results given in Tables 14, 15 and 16 show that the treatment based on extract E2 according to the invention restores the 3 proteasome activities significantly when the treatment is carried out after irradiation. This complete restoration of the proteasome activities indicates that the agent based on Ph has a restorative action on the effects of UVA+UVB in terms of the proteasome activity.

As seen in 3.1), for the NHK treated with extract E2 according to the invention, the amount of intracellular oxidized proteins is smaller than in the reference sample (cf. FIG. 13, lanes 1 and 2). This shows that the stimulating effect observed when using extract E2 according to the invention on the peptidase activities of the proteasome is represented by a decrease in the proportion of intracellular oxidized proteins. Lanes 3 and 4 of FIG. 4 show that UV irradiation does indeed generate a greater amount of oxidized proteins (proportional to the intensity of the spots), but this amount is considerably reduced after using said extract according to the invention.

EXAMPLE 1

Anti-Ageing Day Cream for the Face

| | |
|---|---|
| Glyceryl stearate + PEG-100 stearate | 6.00% |
| Squalane | 3.00% |
| Hydrogenated polyisobutene | 3.00% |
| Glycerol tricaprylate/caprate | 3.00% |
| Glycerol | 2.00% |
| Octyl methoxycinnamate | 2.00% |
| Beeswax | 1.50% |
| Cetostearyl octanoate | 1.50% |
| Cetyl alcohol | 1.00% |
| Stearyl alcohol | 1.00% |
| Dimethicone | 1.00% |
| Extract E2 of alga Phaeodactylum tricornutum, of Example 1.2 | 1.00% |
| Xanthan gum | 0.20% |
| Carbomer | 0.15% |
| Neutralizer | qs |
| Preservatives | qs |
| Perfume, colorants | qs |
| Water | qsp 100.00% |

EXAMPLE 2

Anti-Wrinkle Emulsion-Gel for the Face

| | |
|---|---|
| Glycerol | 5.00% |
| Caprylic/capric/succinic triglycerides | 3.00% |
| Extract E2 of Example 1.2 | 2.00% |
| Octyl methoxycinnamate | 1.00% |
| Crosslinked polymer: $C_{10-30}$-alkyl acrylates/acrylate | 0.50% |
| Wheat protein hydrolyzate | 0.50% |
| Dimethicone copolyol | 0.50% |
| Neutralizer | qs |
| Preservatives | qs |
| Perfume, colorants | qs |
| Water | qsp 100.00% |

EXAMPLE 3

Firming Emulsion for the Body

| | |
|---|---|
| Octyl palmitate | 7.00% |
| Glycerol tricaprylate/caprate | 3.00% |
| Octyl octanoate | 2.00% |
| Phenyl trimethicone | 2.00% |
| Glycerol | 2.00% |
| Stearic acid | 1.00% |
| Sorbitan stearate 20 EO | 0.90% |
| Cetyl alcohol | 0.50% |
| Stearyl alcohol | 0.50% |
| Extract E2 of Example 1.2 | 0.50% |
| Carbomer | 0.40% |
| Xanthan gum | 0.20% |
| Sorbitan stearate | 0.10% |
| Neutralizer | qs |
| Preservatives | qs |
| Perfume, colorants | qs |
| Water | qsp 100.00% |

EXAMPLE 4

Anti-Wrinkle Emulsion-Gel for the Face

| | |
|---|---|
| Glycerol | 5.00% |
| Caprylic/capric/succinic triglycerides | 3.00% |
| Octyl methoxycinnamate | 1.00% |
| Crosslinked polymer: $C_{10-30}$-alkyl acrylates/acrylate | 0.50% |
| Wheat protein hydrolyzate | 0.50% |
| Dimethicone copolyol | 0.50% |
| Extract E2 of Example 1.2 | 0.01% |
| Neutralizer | qs |
| Preservatives | qs |
| Perfume, colorants | qs |
| Water | qsp 100.00% |

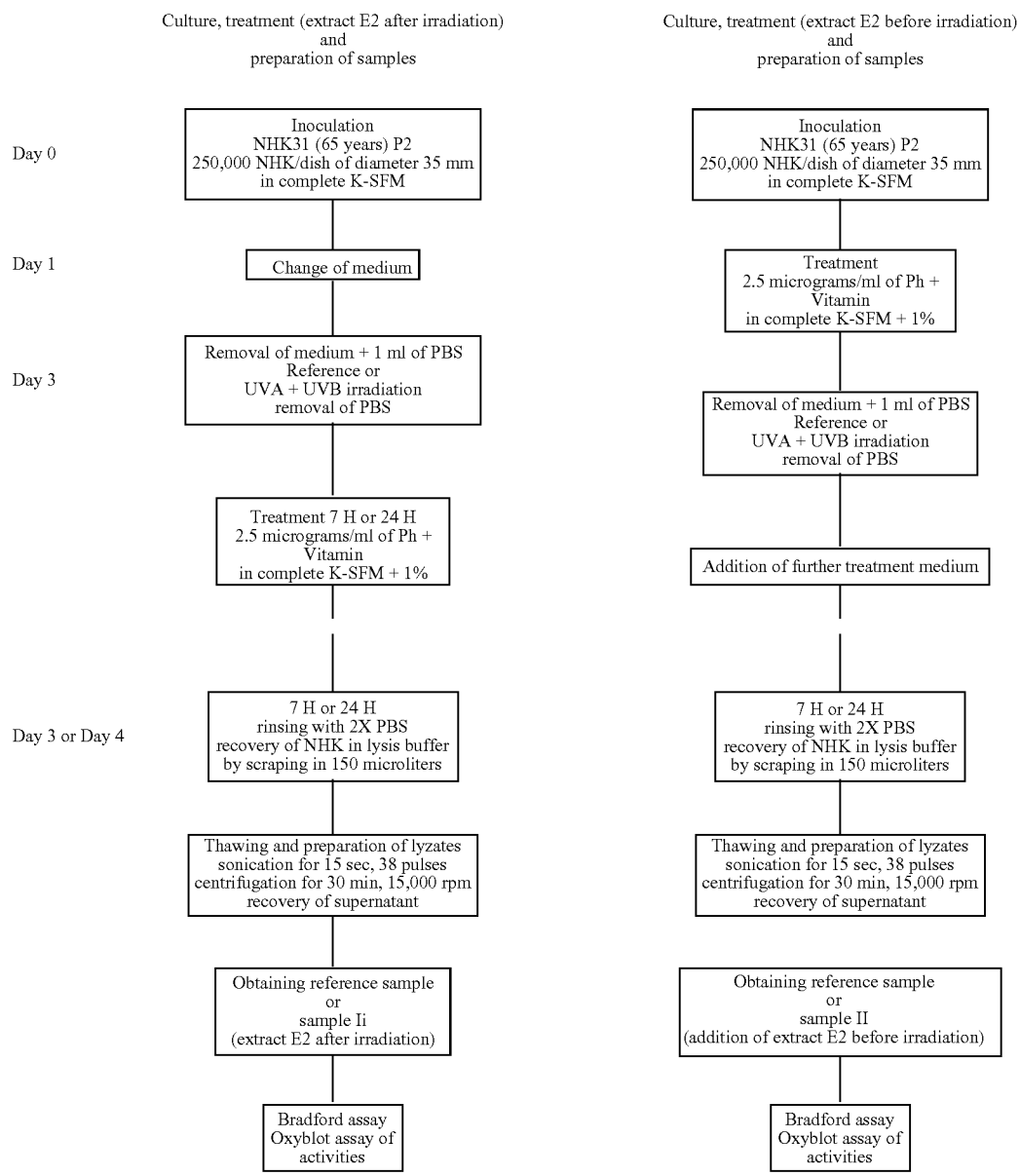
Scheme 1
TABLE 8
(Measurement of the LLVY activity of the proteasome derived from NHK after treatment with extract E2 according to the invention)
| Sample | | Protein in µg/µl | | Rate in FU/min | Activity in pmol/min/mg of protein | | t test p** | |
|---|---|---|---|---|---|---|---|---|
| | | mean | standard deviation | | mean | standard deviation | /ref. UV− | /ref. UV+ |
| Reference | 20 µl | 1.540 | | 480.00 | 90.96 | | | |
| | 20 µl | 1.373 | | 418.80 | 89.02 | 91.27 ± 6.75 | | |
| | 20 µl | 1.599 | 1.500 ± 0.096 | 551.04 | 100.57 | | | |
| | 20 µl | 1.488 | | 431.03 | 84.55 | | | |
| | 20 µl | 1.521 | | 555.11 | 106.53 | | | |

TABLE 8-continued (Measurement of the LLVY activity of the proteasome derived from
NHK after treatment with extract E2 according to the invention)

| Sample | | Protein in μg/μl mean | Protein in μg/μl standard deviation | Rate in FU/min | Activity in pmol/min/mg of protein mean | Activity in pmol/min/mg of protein standard deviation | t test p** /ref. UV− | t test p** /ref. UV+ |
|---|---|---|---|---|---|---|---|---|
| Extract E2 5 μg/ml | 20 μl 20 μl 20 μl | 1.544 1.535 1.599 | 1.550 ± 0.034 | 553.17 515.22 545.13 | 104.60 97.98 99.49 | 102.15 ± 4.07 | 0.0329 S | |

**Significant (S) if the value of p is ≦ 0.05/0.2919X × FU/min for a 15 μl aliquot

TABLE 9

(Measurement of the LLE activity of the proteasome derived from
NHK after treatment with extract E2 according to the invention)

| Sample | | Protein in μg/μl mean | Protein in μg/μl standard deviation | Rate in FU/min | Activity in pmol/min/mg of protein mean | Activity in pmol/min/mg of protein standard deviation | t test p** /ref. UV− | t test p** /ref.UV+ |
|---|---|---|---|---|---|---|---|---|
| Reference | 20 μl 20 μl 20 μl 20 μl 20 μl | 1.540 1.373 1.599 1.488 1.521 | 1.500 ± 0.096 | 357.29 340.57 425.01 322.79 424.63 | 191.97 205.24 219.92 179.52 231.03 | 199.16 ± 17.37 | | |
| Extract E2 5 μg/ml | 20 μl 20 μl 20 μl | 1.544 1.535 1.599 | 1.550 ± 0.034 | 425.65 345.36 387.58 | 228.20 186.20 200.55 | 211.50 ± 21.76 | 0.4097 S | |

**Significant (S) if the value of p is ≦ 0.05/1.3794X ×FU/min for a 15 μl aliquot

TABLE 10

(Measurement of the LSTR activity of the proteasome derived from
NHK after treatment with extract E2 according to the invention)

| Sample | | Protein in μg/μl mean | Protein in μg/μl standard deviation | Rate in FU/min | Activity in pmol/min/mg of protein mean | Activity in pmol/min/mg of protein standard deviation | t test p** /ref. UV− | t test p** /ref. UV+ |
|---|---|---|---|---|---|---|---|---|
| Reference | 20 μl 20 μl 20 μl 20 μl | 1.540 1.373 1.599 1.488 | 1.500 ± 0.096 | 951.85 885.25 1104.90 864.47 | 204.36 213.17 228.45 192.11 | 209.53 ± 15.29 | | |
| Extract E2 5 μg/ml | 20 μl 20 μl 20 μl 20 μl | 1.521 1.544 1.535 1.599 | 1.550 ± 0.034 | 1141.60 1142.90 1092.00 1101.50 | 248.19 244.84 235.26 227.75 | 239.01 ± 9.29 | 0.0165 S | |

**Significant (S) if the value of p is ≦ 0.05/0.3307X × FU/min for a 35 μl aliquot

TABLE 11

(Measurement of the LLVY activity of the proteasome of NHK pretreated with
extract E2 according to the invention 24 h before UVA and UVB irradiation)

| Sample | | Protein in μg/μl mean | Protein in μg/μl standard deviation | Rate in FU/min | Activity in pmol/min/mg of protein mean | Activity in pmol/min/mg of protein standard deviation | t test p** /ref. UV− | t test p** /ref. UV+ |
|---|---|---|---|---|---|---|---|---|
| Reference | 20 μl 20 μl 20 μl 20 μl | 1.038 1.030 1.311 1.232 | 1.153 ± 0.141 | 260.82 363.22 351.97 392.97 | 54.99 77.22 58.76 69.80 | 63.66 ± 10.19 | | |

TABLE 11-continued (Measurement of the LLVY activity of the proteasome of NHK pretreated with extract E2 according to the invention 24 h before UVA and UVB irradiation)

| Sample | | Protein in μg/μl | | Rate in FU/min | Activity in pmol/min/mg of protein | | t test p** | |
|---|---|---|---|---|---|---|---|---|
| | | mean | standard deviation | | mean | standard deviation | /ref. UV− | /ref. UV+ |
| Reference + UV | 20 μl | 1.407 | | 253.25 | 39.39 | 37.08 ± 3.27 | 0.0224 | |
| | 20 μl | 1.444 | 1.426 ± 0.026 | 229.26 | 34.76 | | S | |
| | 20 μl | 0.998 | | 514.70 | 112.94 | | | |
| Extract E2 5 μg/ml | 20 μl | 1.121 | | 458.06 | 89.41 | | | |
| | 20 μl | 1.326 | 1.203 ± 0.173 | 474.78 | 78.36 | 96.90 ± 15.88 | 0.0152 | |
| | 20 μl | 1.365 | | 666.44 | 106.90 | | S | |
| | 20 μl | 1.264 | | 329.56 | 57.06 | | | |
| Extract E2 + UV | 20 μl | 1.322 | 1.255 ± 0.073 | 283.15 | 46.88 | | | |
| | 20 μl | 1.151 | | 369.35 | 70.23 | 60.53 ± 10.76 | 0.5522 | 0.0458 |
| | 20 μl | 1.284 | | 398.45 | 67.95 | | NS | S |

**Significant (S) if the value of p is ≤ 0.05/0.2189X × FU/min for a 20 μl aliquot

TABLE 12

(Measurement of the LLE activity of the proteasome of NHK pretreated with extract E2 according to the invention 24 h before UVA and UVB irradiation)

| Sample | | Protein in μg/μl | | Rate in FU/min | Activity in pmol/min/mg of protein | | t test p** | |
|---|---|---|---|---|---|---|---|---|
| | | mean | standard deviation | | mean | standard deviation | /ref. UV− | /ref. UV+ |
| Reference | 20 μl | 1.038 | | 256.79 | 255.90 | | | |
| | 20 μl | 1.030 | 1.153 ± 0.141 | 377.91 | 379.75 | | | |
| | 20 μl | 1.311 | | 373.48 | 294.67 | 310.11 ± 53.70 | | |
| | 20 μl | 1.232 | | 403.79 | 338.98 | | | |
| Reference + UV | 20 μl | 1.407 | | 271.40 | 199.51 | 192.42 ± 10.02 | 0.0368 | |
| | 20 μl | 1.444 | 1.426 ± 0.026 | 258.62 | 185.34 | | S | |
| | 20 μl | 0.998 | | 532.71 | 552.47 | | | |
| Extract E2 5 μg/ml | 20 μl | 1.121 | | 491.76 | 453.70 | | | |
| | 20 μl | 1.326 | 1.203 ± 0.173 | 595.53 | 464.55 | 493.35 ± 44.66 | 0.0024 | |
| | 20 μl | 1.365 | | 663.05 | 502.67 | | S | |
| | 20 μl | 1.264 | | 335.07 | 274.17 | | | |
| Extract E2 + UV | 20 μl | 1.322 | 1.255 ± 0.073 | 315.22 | 246.69 | | | |
| | 20 μl | 1.151 | | 381.19 | 342.55 | 295.46 ± 43.12 | 0.5489 | 0.0342 |
| | 20 μl | 1.284 | | 395.07 | 318.43 | | NS | S |

**Significant (S) if the value of p is ≤ 0.05/1.0346X × FU/min for a 20 μl aliquot

TABLE 13

(Measurement of the LSTR activity of the proteasome derived from NHK pretreated with extract E2 according to the invention 24 h before UVA and UVB irradiation)

| Sample | | Protein in μg/μl | | Rate in FU/min | Activity in pmol/min/mg of protein | | t test p** | |
|---|---|---|---|---|---|---|---|---|
| | | mean | standard deviation | | mean | standard deviation | /ref. UV− | /ref. UV+ |
| Reference | 50 μl | 1.038 | | 577.08 | 128.68 | | | |
| | 50 μl | 1.030 | 1.153 ± 0.141 | 789.09 | 177.42 | | | |
| | 50 μl | 1.311 | | 789.96 | 139.46 | 148.52 ± 21.51 | | |
| | 50 μl | 1.232 | | 844.41 | 158.62 | | | |
| Reference + UV | 50 μl | 1.407 | | 564.46 | 92.85 | 87.33 ± 7.80 | 0.0181 | |
| | 50 μl | 1.444 | 1.426 ± 0.026 | 510.24 | 81.82 | | S | |
| | 50 μl | 0.998 | | 1079.40 | 250.48 | | | |
| Extract E2 5 μg/ml | 50 μl | 1.121 | | 1001.40 | 206.73 | | | |
| | 50 μl | 1.326 | 1.203 ± 0.173 | 1110.60 | 193.85 | 216.29 ± 24.28 | 0.0069 | |
| | 50 μl | 1.365 | | 1262.10 | 214.10 | | S | |

TABLE 13-continued (Measurement of the LSTR activity of the proteasome derived from NHK pretreated with extract E2 according to the invention 24 h before UVA and UVB irradiation)

| Sample | Protein in μg/μl | | | Rate in FU/min | Activity in pmol/min/mg of protein | | t test p** | |
|---|---|---|---|---|---|---|---|---|
| | | mean | standard deviation | | mean | standard deviation | /ref. UV− | /ref. UV+ |
| Extract E2 + UV | 50 μl | 1.264 | | 682.00 | 124.87 | | | |
| | 50 μl | 1.322 | 1.255 ± 0.073 | | | | | |
| | 50 μl | 1.151 | | 771.19 | 155.07 | 140.49 ± 15.13 | 0.5041 | 0.0214 |
| | 50 μl | 1.284 | | 784.76 | 141.53 | | NS | S |

**Significant (S) if the value of p is ≦ 0.05/0.2315X × FU/min for a 50 μl aliquot

TABLE 14

(Measurement of the LLVY activity of the proteasome of NHK 7 h after UVA + UVB irradiation followed by treatment with extract E2 according to the invention)

| Sample | Protein in μg/μl | | | Rate in FU/min | Activity in pmol/min/mg of protein | | t test p** | |
|---|---|---|---|---|---|---|---|---|
| | | mean | standard deviation | | mean | standard deviation | /ref. UV− | /ref. UV+ |
| Reference | 20 μl | 0.320 | | 532.43 | | | | |
| | 20 μl | 0.563 | 0.697 ± 0.321 | 475.60 | 184.89 | | | |
| | 20 μl | 0.857 | | 448.06 | 114.47 | 142.53 ± 37.32 | | |
| | 20 μl | 1.050 | | 614.88 | 128.24 | | | |
| | 20 μl | 0.967 | | 219.93 | 49.81 | | | |
| Reference + UV | 20 μl | 1.067 | 1.105 ± 0.172 | 211.11 | 43.29 | | | |
| | 20 μl | 1.032 | | 255.43 | 54.19 | 51.37 ± 6.38 | 0.0043 | |
| | 20 μl | 1.355 | | 360.17 | 58.18 | | S | |
| | 20 μl | 0.466 | | 793.98 | | | | |
| Extract E2 5 μg/ml | 20 μl | 0.486 | 0.677 ± 0.237 | 703.83 | | 189.35 ± 17.79 | 0.2090 | |
| | 20 μl | 0.815 | | 752.11 | 201.93 | | NS | |
| | 20 μl | 0.940 | | 758.93 | 176.77 | | | |
| | 20 μl | 1.257 | | 846.29 | 147.35 | | | |
| Extract E2 + UV | 20 μl | 1.334 | 1.248 ± 0.100 | 806.37 | 132.29 | | | |
| | 20 μl | 1.106 | | 849.40 | 168.13 | 163.40 ± 31.88 | 0.4600 | 0.0005 |
| | 20 μl | 1.296 | | 1218.50 | 205.84 | | NS | S |

**Significant (S) if the value of p is ≦ 0.05/0.2189X × FU/min for a 20 μl aliquot

TABLE 15

(Measurement of the LSTR activity of the proteasome derived from NHK 7 h after UVA + UVB irradiation followed by treatment with extract E2 according to the invention)

| Sample | Protein in μg/μl | | | Rate in FU/min | Activity in pmol/min/mg of protein | | t test p** | |
|---|---|---|---|---|---|---|---|---|
| | | mean | standard deviation | | mean | standard deviation | /ref. UV− | /ref. UV+ |
| Reference | 40 μl | 0.320 | | 1115.40 | | | | |
| | 40 μl | 0.563 | 0.697 ± 0.321 | 966.14 | | | | |
| | 40 μl | 0.857 | | 821.07 | 316.91 | 318.86 ± 2.75 | | |
| | 40 μl | 1.050 | | 1163.50 | 320.80 | | | |
| | 40 μl | 0.967 | | 463.17 | 158.48 | | | |
| Reference + UV | 40 μl | 1.067 | 1.105 ± 0.172 | 498.85 | 154.55 | | | |
| | 40 μl | 1.032 | | 534.34 | 171.26 | 161.03 ± 7.18 | 0.0000 | |
| | 40 μl | 1.355 | | 748.43 | 159.84 | | S | |
| | 40 μl | 0.466 | | 1354.50 | | | | |
| Extract E2 5 μg/ml | 40 μl | 0.486 | 0.677 ± 0.237 | 1383.60 | | 397.08 ± 24.86 | 0.0475 | |
| | 40 μl | 0.815 | | 1168.20 | 414.67 | | S | |
| | 40 μl | 0.940 | | 1232.40 | 379.50 | | | |
| | 40 μl | 1.257 | | 1326.90 | 305.44 | | | |
| Extract E2 + UV | 40 μl | 1.334 | 1.248 ± 0.100 | 1228.40 | 266.43 | | | |
| | 40 μl | 1.106 | | 1276.10 | 333.94 | 314.44 ± 37.30 | 0.8824 | 0.0002 |
| | 40 μl | 1.296 | | 1575.90 | 351.96 | | NS | S |

**Significant (S) if the value of p is ≦ 0.05/0.2894X × FU/min for a 40 μl aliquot

TABLE 16

(Measurement of the LLE activity of the proteasome derived from NHK 7 h after UVA + UVB irradiation followed by treatment with extract E2 according to the invention)

| Sample | | Protein in µg/µl | | Rate in FU/min | Activity in pmol/min/mg of protein | | t test p** | |
|---|---|---|---|---|---|---|---|---|
| | | mean | standard deviation | | mean | standard deviation | /ref. UV− | /ref. UV+ |
| Reference | 20 µl | 0.320 | | 446.80 | | | | |
| | 20 µl | 0.563 | 0.697 ± 0.321 | 429.01 | | | | |
| | 20 µl | 0.857 | | 391.07 | 472.22 | 474.49 ± 3.21 | | |
| | 20 µl | 1.050 | | 483.67 | 476.76 | | | |
| | 20 µl | 0.967 | | 183.97 | 196.93 | | | |
| Reference + UV | 20 µl | 1.067 | 1.105 ± 0.172 | 177.14 | 171.70 | | | |
| | 20 µl | 1.032 | | 218.01 | 218.60 | 204.81 ± 26.39 | 0.0002 | |
| | 20 µl | 1.355 | | 303.89 | 232.02 | | S | |
| | 20 µl | 0.466 | | 588.98 | | | | |
| Extract E2 5 µg/ml | 20 µl | 0.486 | 0.677 ± 0.237 | 542.38 | | | | |
| | 20 µl | 0.815 | | 598.25 | 759.17 | 671.61 ± 123.83 | 0.1533 | |
| | 20 µl | 0.940 | | 530.53 | 584.05 | | NS | |
| | 20 µl | 1.257 | | 576.40 | 474.34 | | | |
| Extract E2 + UV | 20 µl | 1.334 | | 598.01 | 463.69 | | | |
| | 20 µl | 1.106 | 1.248 ± 0.100 | 637.05 | 595.98 | 534.53 ± 75.84 | 0.3509 | 0.0002 |
| | 20 µl | 1.296 | | 756.61 | 604.10 | | S | S |

**Significant (S) if the value of p is ≦ 0.05/1.0346X × FU/min for a 20 µl aliquot

Figure 1:
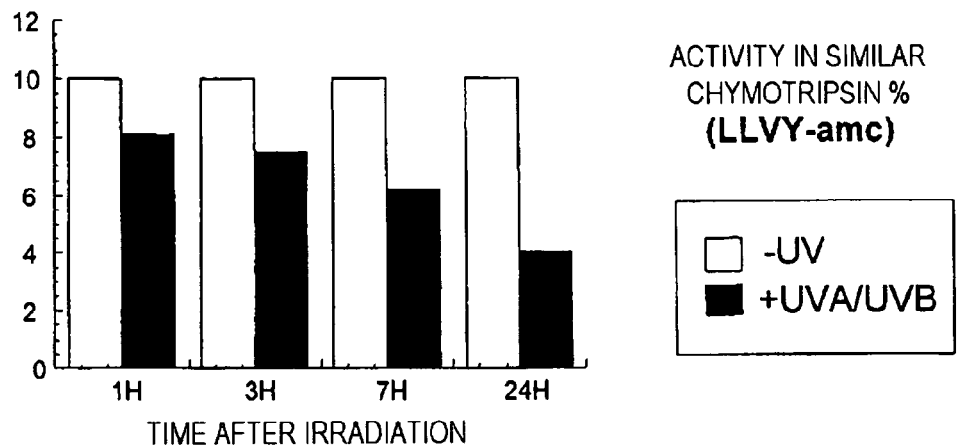
FIG. 1 illustrates that the peptidase activity of NHK in primary culture with the substrate LLVY-amc is reduced for the four times analyzed after UVA+UVB exposure.
Figure 2:
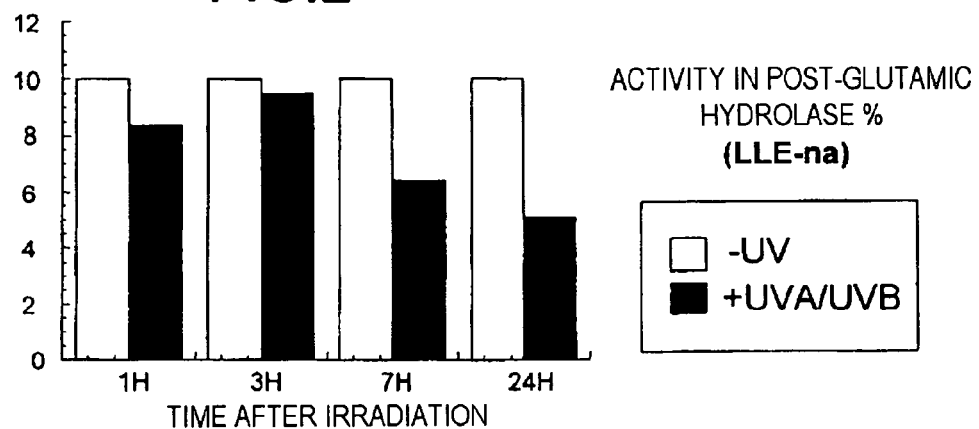
FIG. 2 illustrates that the peptidase activity of NHK in primary culture with the substrate LLE-na is reduced for the four times analyzed after UVA+UVB exposure.
Figure 3:
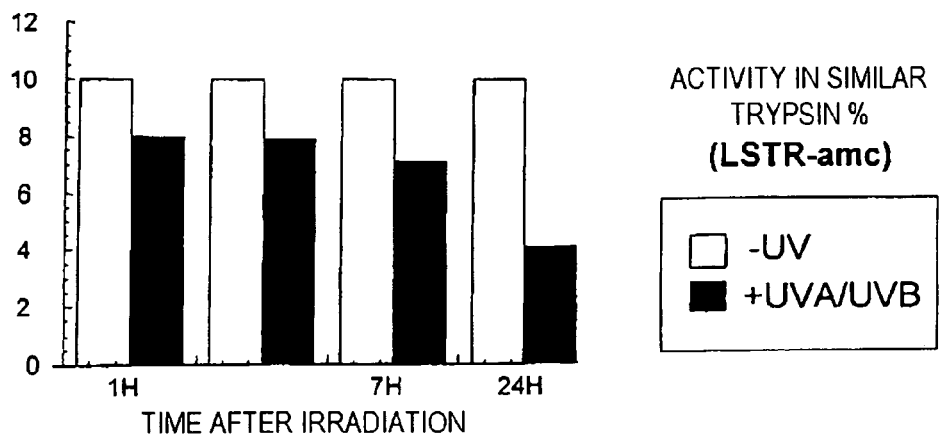
FIG. 3 illustrates that the peptidase activity of NHK in primary culture with the substrate LSRT-amc is reduced for the four times analyzed after UVA+UVB exposure.
Figure 4:
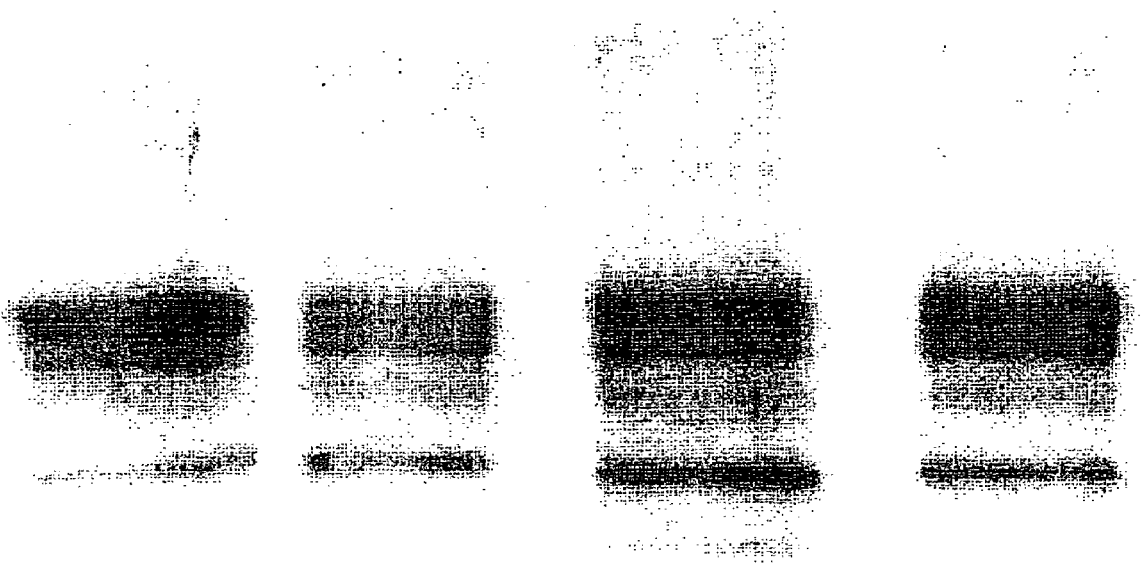
FIG. 4 illustrates that in the NHK treated with Ph for 7 hours, the amount of intracellular oxidized proteins is smaller than for the reference cells.

The invention claimed is:

1. A method of cosmetic skin care selected from delaying appearance of skin aging effects, treating of skin aging, improving the firmness of the skin, improving elasticity of the skin, delaying the appearance of wrinkles, and reducing the depth of wrinkles, comprising topically applying to the skin of a person in need thereof a cosmetically effective amount of an extract of Alga *Phaeodactylum* obtained by extraction with a polar extraction solvent.

2. The method of claim 1, wherein the polar extraction solvent is a $C_1$-$C_6$ alcohol, a water/$C_1$-$C_6$ alcohol mixture, a $C_2$-$C_6$ polyhydric alcohol or a $C_3$-$C_6$ ester of an organic acid.

3. The method of claim 1, wherein the extract is obtained by extraction of the Alga *Phaeodactylum* with an alcohol or a water/alcohol mixture.

4. The method of claim 3, wherein said alcohol or water/alcohol mixture has been rendered alkaline.

5. The method of claim 1, wherein the extract is obtained by extraction of the Alga *Phaeodactylum* with an alcohol or a water/alcohol mixture, wherein the alcohol is isopropanol, ethanol, methanol or a mixture thereof.

6. The method of claim 1, wherein the extract is obtained by extraction of the Alga *Phaeodactylum* with ethanol.

7. The method of claim 1, wherein the extract is obtained by extraction of the Alga *Phaeodactylum* with isopropanol.

8. The method of claim 1, wherein the Alga *Phaeodactylum* is frozen before it is extracted, after which it is brought into contact with the extraction solvent.

9. The method of claim 8, wherein the extraction is performed by immersing the frozen Alga *Phaeodactylum* directly in the extraction solvent, which has been heated.

10. The method of claim 1, wherein before any extraction operation, the Alga *Phaeodactylum* is macerated in the extraction solvent at room temperature.

11. The method of claim 10, wherein the Alga *Phaeodactylum* is macerated for a period of about 5 minutes and 80 minutes.

12. The method of claim 9, wherein the extraction is carried out in the heated extraction solvent under reflux.

13. The method of claim 1, wherein the extraction is carried out under an inert atmosphere.

14. The method of claim 1, wherein the extract is obtained by:

a) freezing and then immersing the Alga *Phaeodactylum* in the polar extraction solvent, which has been heated, said extraction solvent being an alcohol or water/alcohol mixture;

b) macerating the Alga *Phaeodactylum* in the extraction solvent at room temperature;

c) rendering the extraction solvent alkaline to a pH of 10 to 14, thereby obtaining an alcoholic or aqueous-alcoholic phase;

d) removing insoluble materials from the alcoholic or aqueous-alcoholic phase;

e) adding substantially distilled water to the alcoholic or aqueous-alcoholic phase, thereby obtaining an aqueous-alcoholic solution;

f) washing the resultant aqueous-alcoholic solution by a liquid-liquid process with an apolar solvent that is substantially immiscible with the alcoholic or aqueous-alcoholic phase;

g) removing the phase containing the apolar solvent;

h) acidifying the aqueous-alcoholic phase received after removal of the phase containing the apolar solvent to a pH of 1 to 3;

i) subjecting the solution obtained after acidification to a liquid-liquid extraction with an apolar solvent that is substantially immiscible with the alcoholic or aqueous-alcoholic phase;

j) then removing the aqueous-alcoholic phase; and k) subjecting the phase containing the apolar solvent, recovered after removal of the aqueous-alcoholic phase, to evaporation to give an oil which is substantially free of apolar solvent, which is the desired *Phaeodactylum* extract.

15. The method of claim 1, wherein the amount of extraction solvent used is 0.1 liter to 20 liters per 100 grams of the Alga *Phaeodactylum*, expressed by dry weight of the Alga *Phaeodactylum*.

16. The method of claim 1, wherein the Alga *Phaeodactylum* extract is an extract of the alga *Phaeodactylum tricornutum*.

17. The method of claim 1, wherein the Alga *Phaeodactylum* extract is incorporated into a cosmetic composition in a concentration of about 0.01% to 10% by weight, based on the total weight of the final composition.

18. The method of claim 1, wherein the Alga *Phaeodactylum* extract is incorporated into a cosmetic composition in a concentration of about 0.1% to 5% by weight, based on the total weight of the final composition.

19. The method of claim 1, which is for delaying appearance of skin aging effects.

20. The method of claim 1, which is for treating of skin aging.

21. The method of claim 1, which is for improving the firmness of the skin.

22. The method of claim 1, which is for improving elasticity of the skin.

23. The method of claim 1, which is for delaying the appearance of wrinkles.

24. The method of claim 1, which is for reducing the depth of wrinkles.

25. A method of cosmetic skin care selected from a skin care before exposure to UV rays and a restorative or reparative skin care after exposure to UV rays, comprising topically applying to the skin of a person in need thereof a cosmetically effective amount of an extract of Alga *phaeodactylum* obtained by extraction with a polar extraction solvent.

26. The method of claim 25, wherein the extract is obtained by extraction of the Alga *Phaeodactylum* with ethanol.

27. The method of claim 25, wherein the Alga *Phaeodactylum* extract is an extract of the alga *Phaeodactylum tricornutum*.

28. The method of claim 25, wherein the Alga *Phaeodactylum* extract is incorporated into a cosmetic composition in a concentration of about 0.01% to 10% by weight, based on the total weight of the final composition.

29. The method of claim 25, wherein the Alga *Phaeodactylum* extract is incorporated into a cosmetic composition in a concentration of about 0.1% to 5% by weight, based on the total weight of the final composition.

* * * * *